United States Patent [19]
Orth et al.

[11] Patent Number: 5,100,392
[45] Date of Patent: Mar. 31, 1992

[54] IMPLANTABLE DEVICE FOR ADMINISTRATION OF DRUGS OR OTHER LIQUID SOLUTIONS

[75] Inventors: Jeffrey L. Orth, Salt Lake City; Richard E. Hoffer, Park City; Philip M. Triolo, Salt Lake City, all of Utah

[73] Assignee: Biosynthesis, Inc., Salt Lake City, Utah

[21] Appl. No.: 447,635

[22] Filed: Dec. 8, 1989

[51] Int. Cl.$^5$ ............................................. A61M 25/00
[52] U.S. Cl. .................................... 604/175; 128/899; 604/93
[58] Field of Search ................. 604/157, 93, 175, 264, 604/891.1; 128/769, 899

[56] References Cited

U.S. PATENT DOCUMENTS

| | | | |
|---|---|---|---|
| 3,313,289 | 4/1967 | Kapral | 604/93 |
| 3,646,616 | 3/1972 | Keshin | 604/175 |
| 3,699,956 | 10/1972 | Kitrilakis et al. | 604/175 |
| 4,069,307 | 1/1978 | Higuchi et al. | |
| 4,180,560 | 12/1979 | Katz et al. | |
| 4,192,308 | 3/1980 | Michaels | |
| 4,207,390 | 6/1980 | Mamajek et al. | |
| 4,217,664 | 8/1980 | Fiaso | 604/175 |
| 4,368,737 | 1/1983 | Ash | 604/175 |
| 4,505,277 | 3/1985 | Klesius | 604/93 |
| 4,557,724 | 12/1985 | Gregonis et al. | |
| 4,624,847 | 11/1986 | Ayer et al. | |
| 4,681,582 | 7/1987 | Yamamoto | |
| 4,684,524 | 8/1987 | Eckenhoff et al. | |
| 4,687,481 | 8/1987 | Nuwayser | |
| 4,723,947 | 2/1988 | Konopka | |
| 4,826,480 | 5/1989 | Diaz et al. | |
| 4,878,895 | 11/1989 | Klesius et al. | 128/899 |
| 4,880,006 | 11/1989 | Albrekisson et al. | 623/66 |

OTHER PUBLICATIONS

Sossen, H. "Insulin Pump Artificial Pancreas", *Medical Electronics*, Jun. 1980, pp. 64–67.
Blackshear, P. J. et al., "Insulin Replacement: Current Concepts", *Trans. Am. Soc. Artif. Intern. Organs*, Fol. 32 (1986) pp. 646–655.
Schade, D. S. et al., "Subcutaneous Peritoneal Access Device for Type 1 Diabetic Patients Nonresponsive to Subcutaneous Insulin", *Diabetes*, vol. 31, May 1982, pp. 470–473.
Schade, D. S. et al., "The Peritoneum-A Potential Insulin Delivery Route for a Mechanical Pancreas", *Diabetes Care* vol. 3, No. 2 (Mar./Apr. 1980) pp. 229–234.
Strum, S. et al., "Improved Methods for Venous Access: The Port-A-Cath, A Totally Implanted Catheter System", *Jr. of Clinical Oncology*, vol. 4, No. 4, Apr. 1986, pp. 596–603.
Mier, A. K. et al., "New Portable Infusion Pump for Prolonged Subcutaneous Administration of Opioid Analgesics in Patients with Advanced Cancer", *British Medical Jr.*, vol. 292 (Jun. 7, 1986), p. 1496.
Brownlee, M. et al., "Glycosylated Insulin Complexed to Concanavalin A: Biochemical Basis for a Closed--Loop Insulin Delivery System", *Diabetes*, vol. 32 (Jun. 1983) pp. 499–504.
Selam, J. L. et al., "Total Implantation of a Remotely Controlled Insulin Minipump in a Human Insulin-Dependent Diabetic", *Artificial Organs*, vol. 6, No. 3 (Aug. 1982) pp. 315–319.
Spencer, W. J. et al., "The Status of Programmable and Implantable Insulin Delivery Systems-The Artificial Pancreas", IEEE 1980 Frontiers of Engineering in Health Care (1980) pp. 162–165.
Chvapil, M. et al., "Development of Topical BAPN Delivery System for Acute Spinal Cord Injury in Dogs", *Jr. of Biomedical Materials Research*, vol. 18, 1984, pp. 757–769.

*Primary Examiner*—Stephen C. Pellegrino
*Assistant Examiner*—Ralph A. Lewis
*Attorney, Agent, or Firm*—Trask, Britt & Rossa

[57] ABSTRACT

An implantable device for administering drugs or other substances to body tissues of a patient is disclosed. The device is designed to allow controlled ingrowth of connective tissue into the device, and a solution may be pumped or injected into the device where the solution is diffused through the ingrown connective tissue and out into the body.

22 Claims, 3 Drawing Sheets

IMPLANTABLE DEVICE FOR ADMINISTRATION OF DRUGS OR OTHER LIQUID SOLUTIONS

BACKGROUND OF THE INVENTION

1. Field of the Invention

This invention relates to implantable devices capable of delivering liquid substances, such as drugs, to the peritoneal cavity or other sites in the body where the device has been implanted. More particularly, this invention relates to implantable devices which are capable of promoting ingrowth of connective tissue and which thereby become incorporated into the tissues of the body.

2. Statement of the Art

The necessity to achieve adequate, safe, and convenient administration of drug therapy to patients, particularly diabetic patients, has lead to the development of devices which deliver a predetermined dosage or amount of drug to the patient over a required amount of time. Initially, these devices were typically extracorporeal units comprising a source or reservoir of drug, a catheter, and a pump for controlled delivery. Recently, research and development in drug delivery devices has been focused on implantable devices which will lead to more convenient drug therapy for patients.

Insulin-dependent diabetic patients, for example, typically have been required to undergo daily injections of insulin. Daily injections often prove to be difficult or unsatisfactory for a number of reasons. For many patients, self-administration of an injection is difficult and they must depend upon another person to give them the injection. The frequency with which subcutaneous injections must be given leads to soreness of the usual injection site. Often, injections of the drug are made peritoneally while the site normally used for injection heals. More importantly, studies have indicated that a single injection in a twenty-four hour period does not provide an optimal or equilibrated dose of insulin to a patient because very high blood levels are initially experienced, leaving inadequate amounts of insulin in the body for later meals, such as lunch and dinner.

For these and other reasons, attempts have been made to develop a device which could produce a controlled and somewhat constant flow of insulin to the patient. Extracorporeal devices were initially developed in which medication was delivered via a catheter permanently or semi-permanently implanted in a vein, in a muscle, or in the peritoneum of the patient (e.g., U.S. Pat. No. 4,723,947 to Konopka). The patient or caregiver typically would preprandially determine an amount of insulin needed, based on the projected amount of caloric intake for the particular meal, and the required amount of drug would be delivered to the patient by injection or pumping means. These devices required the patient to carry the necessary equipment of the device on or near his or her person, such as on a specialized belt.

Other extracorporeal devices were developed, such as the transdermal patch filled with drug, which, when affixed to the wearer's skin, would slowly diffuse drug through the skin and into the body (e.g., U.S. Pat. No. 4,687,481 to Nuwayser). Despite the success achieved in delivering a more suitable dosage of drug pursuant to the patient's immediate needs, the obvious inconvenience of extracorporeal drug delivery devices lead to the development of implantable devices.

Delivering a medication, such as insulin, into the body via an implantable device has been approached in several different ways. For example, devices have been developed where the patient ingests a predetermined dose of medication enveloped in a special covering which expands upon contact with body fluids thereby keeping the device within the body long enough to effect a long-term administration of the medication. (U.S. Pat. No. 4,207,390 to Mamajek)

More frequently, implantable devices have been developed which must be surgically inserted into a body cavity of the patient. Examples of such devices are disclosed in U.S. Pat. No. 4,069,307 to Higuchi, et al. (ethylene-vinyl acetate copolymer reservoir of drug which operates by diffusion); U.S. Pat. No. 4,180,560 to Katz et al. (spherical implantable pellets); U.S. Pat. No. 4,557,724 to Gregonis, et al. (refillable implantable reservoir of drug placed in contact with peritoneal cavity); U.S. Pat. No. 4,624,847 to Ayer et al. (osmotic dispensing device implantable in the peritoneal cavity); U.S. Pat. No. 4,684,524 to Eckenhoff et al. (implantable dispenser of heat-responsive composition diffused by osmotic processes); U.S. Pat. No. 4,826,480 to Diaz et al. (implantable catheter).

A common problem encountered with implantable devices has been overgrowth of the device by dense fibrotic tissue having little or no vascularization—a process called "encapsulation." More specifically, encapsulation occurs when a foreign object is placed in the body. Connective tissue begins to grow about the foreign object, and as the connective tissue matures, it loses its vascularization and becomes thick scar tissue. Encapsulation of implantable devices results in either occlusion of the drug outlet system or overgrowth of the entire device so that no drug can escape the encapsulated area. Encapsulation is particularly troublesome where only a small flow of drug is being delivered through the device.

Because encapsulation typically occurs where there is a continuous surface upon which the tissue can migrate, different approaches have been taken to limit or inhibit encapsulation of implanted devices. For example, the shape of some implantable devices has been modified to reduce sharp edges which, it appears, tend to enhance encapsulation. Materials which discourage encapsulation have been used preferentially. Even with attention to design parameters, however, encapsulation of implantable devices has proved to be the limiting factor in efficacy of implantable devices.

SUMMARY OF THE INVENTION

The present invention is directed to an implantable device for administering solutions, such as medications or nutrients, to the peritoneal cavity, or other appropriate site, of a patient. In contrast to prior devices, however, the invention makes use of the natural proliferation of connective tissue, and encourages controlled growth of connective tissue into the device while discouraging encapsulation.

The device generally includes an outer casing made of porous synthetic material, the pore size of which may range from about 60 microns to about 500 microns, with a preferred pore size ranging from about 160 to 300 microns. Pore sizes in this range allow vascularized connective tissue to grow into and through the pores of the outer casing from the surrounding tissue environment, but do not allow uncontrolled growth of tissue which leads to encapsulation.

The design of the outer casing permits connective tissue to continue to grow normally thereby precluding an inflammatory response with the foreign material. More particularly, when growing tissue is irritated by movement or contact with a foreign object, the tissue begins to thicken, and it eventually becomes under-vascularized scar tissue. An advantageous feature of this invention is that the design does not allow tissue inside of the device to move and, as a result, tissue grows normally with full vascularization.

The outer casing defines an inner space which eventually becomes filled with vascularized connective tissue growing inwardly through the pores of the outer casing. To an opening in the outer casing is connected an inlet catheter through which the solution for administration is injected or pumped. The injected solution passes through the inlet catheter and into the inner space now filled with ingrown connective tissue. There, the solution encounters the connective tissue and a diffusion gradient is formed. The solution diffuses into interstitial spaces which are naturally formed in the connective tissue, and is diffused to nearby capillaries. The substance is then distributed by the vascular system to the tissues of the patient.

In an alternative embodiment of the device, a plurality of hollow tubules made from a synthetic material capable of diffusing substances therethrough are positioned within the inner space formed by the outer casing. The synthetic material of the tubules may typically allow only molecules having less than a molecular weight of 100,000 to pass therethrough. As a result, connective tissue is not able to grow through the synthetic material of the tubules. The synthetic material may also be incapable of allowing blood cell components to pass therethrough. As a result, drugs or substances which cause an antigenic response in the body, but which have particular properties important to administration of a desired drug or solution, may be used safely. For example, Concanavalin A, a glucose-binding lectin molecule which is antigenic in the body, may be bound with three insulin molecules and one sepharose (a saccharide) molecule. Glucose molecules circulating in the blood can pass through the connective tissue in the device and through the synthetic material of the inner tubules, replacing the insulin molecules on Concanavalin A. But the sepharose bound Concanavalin A molecule will be too large to pass through the material of the tubules, and will not come in contact with any blood cellular components to set up an antigenic response. Such blood cellular components would include leukocytes (white blood corpuscles) and lymphocytes. Similarly, cultured non-autogenous pancreatic islet cells which produce insulin, may be injected into the inner tubules with the result that glucose molecules passing through the material of the tubules will trigger release of insulin from the islet cells, but blood components will not come in contact with the non-autogenous islet cells to produce an antigenic response.

In this embodiment, connective tissue grows through the pores of the outer casing and invades the inner space formed therein, and between the individual tubules, only until it contacts the material of the tubules. The tubules have at least one open end each. Typically, a collecting member, such as an end cap, is mechanically associated with the open ends of the tubules. The substance to be administered is injected into an inlet catheter which may be connected to the collecting member, and the substance passes from the inlet catheter, into the collecting member, and into the open end of the tubules. The substance diffuses through the material of the tubules, and is taken up by the connective tissue surrounding the tubules.

In an alternative embodiment, the outer casing may be formed from a solid piece of porous synthetic material through which has been formed linear passageways, such as by drilling. The linear passageways may then be fitted with tubules made of synthetic material, capable of diffusing molecules therethrough, as previously described. In this embodiment, connective tissue will grow into the pores of the solid outer casing until the connective tissue contacts the material of the tubules.

In another alternative embodiment, there may be only one tube positioned within the outer casing thereby forming an inner casing defining a chamber. As with the smaller tubules, the inner casing is made of a synthetic material capable of diffusing molecules having a molecular weight of up to 100,000 therethrough, but prohibiting growth of connective tissue therethrough. In this embodiment, the inner chamber may serve as a reservoir for the substance to be administered. The inner casing may have either one opening or two.

The device may be coated with collagen, collagen and fibroblasts or with tissue growth-enhancing substances in order to promote the proliferation of certain types of tissue around and into the device.

The implantable device may be made in any shape which does not have sharp corners or aspects (which tend to promote encapsulation). The size of the device is dependent upon many factors including the size, weight and age of the patient, the amount of solution to be administered, and the type of solution or drug to be administered. The shape of the device may also be dependent upon where the device is to be placed in the patient's body. Based on these and other criteria, the volume of the device may be from about two cubic centimeters to about forty cubic centimeters.

Any drug or liquid solution having a molecular size small enough to pass through the synthetic material of the tubules or inner casing may be used.

DETAILED DESCRIPTION OF THE PREFERRED EMBODIMENTS

Figure 1:
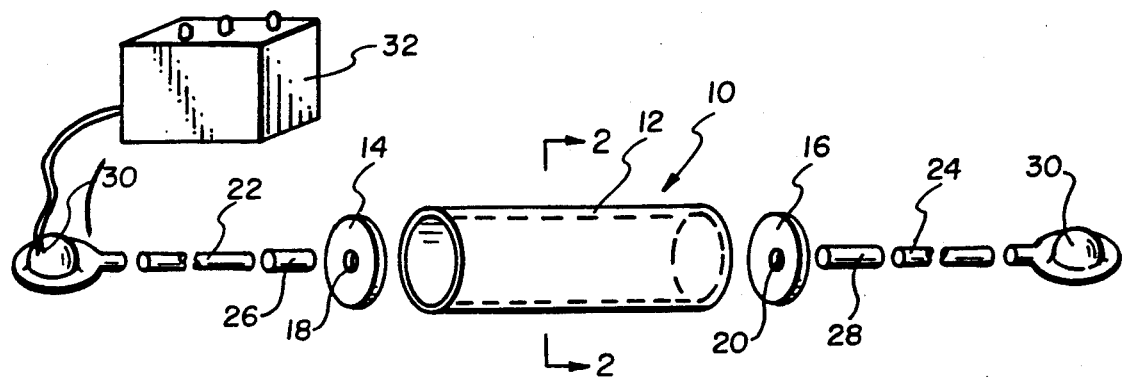
FIG. 1 is an exploded perspective view of the device.

A preferred embodiment of the invention herein is illustrated in FIG. 1 in which the main body of the device, generally at 10, is shown to include an outer casing 12 of material formed into a hollow tube having an opening at either end. The outer casing 12 of the device may be made of any porous synthetic material having a pore size capable of allowing connective tissue from the surrounding environment to grow through the pores of the material. Pore size, for the purposes of this invention, should range from about 60 to about 500 microns, and preferably from about 160 microns to about 300 microns. The pores of the material selected may be of a regular conformation, such as a mesh or woven fabric, or may be of an irregular conformation, such as is found in the product Medpor ® (Porex, Inc., Fairburn, Ga.). Medpor ® is a high density polyethylene material having an intricate network of omnidirectional pores with irregular conformation.

Any type of porous synthetic material may be used which is non-antigenic and inert in the body. For the purposes of this invention, "synthetic" means any material which is manufactured and not naturally occurring; "synthetic" materials may therefore include inert metals, polymers of rubber or plastic, and naturally occurring materials, such as collagen, which may be manufactured and/or treated for use in the invention. Polyethylene is a particularly suitable material for use in this invention because of its inert properties.

The outer casing or tube of the device is closed at either end by means of a collecting member 14, 16, or end cap. The collecting members are attached to the ends of the outer casing by means of an adhesive. When using polyethylene as the outer casing for the device, special surgical adhesives may be necessary for affixing the collecting members to the outer casing, given the particular inert properties of polyethylene. Any adhesive which produces an airtight mechanical bond between the end cap and the outer casing may be used. Adhesives which will allow bonding to polyethylene include TRA-Bond FDA 2LY Resin and hardener (TRA-Con, Inc., Medford, Mass). Additionally, bonding to polyethylene may be achieved by heating or ultrasonic treatment.

The collecting members 14, 16, or end caps, have an aperture 18, 20 for placement of an inlet catheter 22 and an outlet catheter 24. The inlet and outlet catheters may be made from any inert non-porous synthetic material, such as polyurethane. The inlet and outlet catheters are connected to the apertures of the collecting members by means of flexible strain relief connectors 26, 28, which may be made from a flexible material, such as silicone rubber, which addresses the flexing strength requirements encountered at the collecting member aperture.

To the inlet catheter may be connected an injection port 30, as illustrated in FIG. 1, which is implanted just below the epidermis of the patient in the region where the device is implanted. Typical injection ports which may be used are Port-a-cath ® (Pharmacia, Inc., Minn.) or Koken Port (Koken Co., Ltd., Tokyo, Japan). An injection port is typically a device comprised of a small reservoir, an exit therefrom, and a self-sealing penetrable septum through which an injection needle is passed to inject the substance.

Alternatively, a pumping device 32 may be attached to the inlet catheter to deliver a controlled amount of drug or substance to the catheter for delivery to the ingrown tissue. The pump 32 may be fitted external to the body or may be implanted within the body.

The device may be implanted in any appropriate body cavity where the drug or substance for administration is optimally delivered. For example, it has been demonstrated, as discussed above, that insulin delivered to the peritoneal cavity interacts with the liver much faster than by other methods. Thus, where the device may be used for administration of insulin to a diabetic patient, implantation in the peritoneal cavity would be appropriate. The device is placed inside the peritoneal cavity just below the peritoneum. The device is covered with omentum recovered from the surrounding area, and the omentum is sutured in place about the outer casing. Omentum is rich in vascularized connective tissue, and provides an ideal environment for ingrowth of connective tissue into the device. Examples of implantation of the device follow:

EXAMPLE 1

The abdomen of the patient is entered by incision. A subcutaneous tunnel is created cranial and/or caudal to the incision. This tunnel penetrates into the abdomen. Subcutaneous pockets are created for the placement of the ports or the pump of the device. The omentum from the surrounding area is exteriorized and wrapped around the device. The omentum is held in place about the device by suturing to itself with absorbable suture. The inlet and/or outlet catheters are withdrawn through the abdominal and subcutaneous tunnels. To the inlet and outlet catheters of the device are attached a port or implantable pump by use of surgical adhesive to engage the catheter end and opening of the pump or port. The ports or pumps, and the catheters to which they are attached, are placed in the subcutaneous pockets and are secured in place. The incision is closed.

EXAMPLE 2

The skin is incised and the subcutaneous tunnels and/or pockets created, as indicated in Example 1. The abdominal cavity is entered using a laparoscope and procedural instrumentation. The device is placed into the abdominal cavity. The catheters are placed so as to exit through the abdominal space into the tunnel. The device is wrapped with omentum and the omentum fixed as in Example 1 above. The catheter ends are each attached to a port or an implantable pump. The ports or pump are placed in the subcutaneous pocket so formed. The laparoscopic site is closed and the skin incision closed.

EXAMPLE 3

The skin of the patient is incised. A subcutaneous pocket and tunnel are created cranial or caudal to the incision. The device is placed in the subcutaneous pocket, and the ports or implantable pump, which have been connected to the catheter ends, as in Example 1, are placed in the tunnels. Placement procedure follows that described in Examples 1 and 2. The incision is closed.

Figure 2:
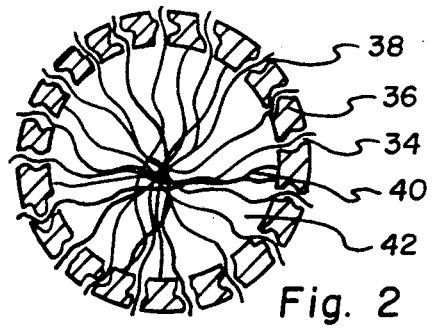
FIG. 2 is a cross-section of the device shown in FIG. 1 taken at line 2—2.

The device is implanted for an amount of time sufficient to allow tissue ingrowth before substance administration is begun. This period of time differs among patients, but is typically not less than two weeks. The rate of ingrowth may be regulated by the ultimate shape and/or dimension of the device. FIG. 2 illustrates the ingrowth of tissue into the device after a sufficient amount of time has passed after implantation. The pores 34 of the outer casing 36 are shown with connective tissue 38 growing therethrough, and connective tissue 40 can be seen to have invaded into the inner space 42 of the device.

Figure 3:
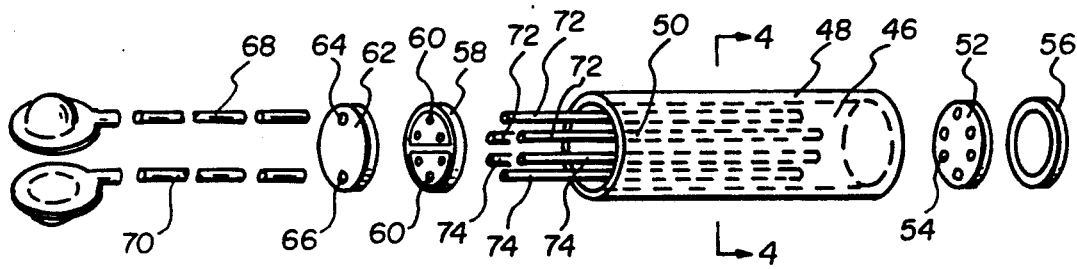
FIG. 3 is an exploded perspective view of an alternative embodiment of the device.

In an alternative embodiment, illustrated in FIG. 3, the inner space 46 formed by the outer casing 48 of porous synthetic material is filled with a bundle of hollow tubules 50 formed from a permeable synthetic material which will allow molecules of a particular size to pass therethrough by diffusion, but will not allow ingrowth of tissue therethrough. Any synthetic material may be used which has the capability of allowing only molecules with a molecular weight of up to 100,000 to pass therethrough. Such synthetic materials may include polysulfone.

In the embodiment illustrated in FIG. 3, the outer casing 48 is fitted at one end with an end plate 52 having apertures 54 formed therein corresponding to the placement of the tubules 50 in the inner space 46. The plate 52 is then covered by means of a collecting member 56, or end cap. At the opposite end of the outer casing, a second plate 58 having apertures 60 therein, corresponding to the placement of the tubules in the inner space, is placed over that end of the outer casing. A second collecting member 62 covers the second plate 58, the second collecting member having two apertures 64, 66 therein for placement of an inlet catheter 68 and outlet catheter 70, respectively.

In operation, the drug or substance is injected or pumped into the inlet catheter 68. The drug passes along the inlet catheter, through the aperture 64 in the second collecting member 62, and is channeled into the open ends of the upper tubules 72 by means of the apertures 60 of the second plate 58. The drug passes through the upper tubules 72 where some of it diffuses through the membrane of the tubules. Any drug not diffused outwardly continues through the upper tubules and through the corresponding apertures 54 of the plate 52 where the drug momentarily pools in the collecting member 56. The drug then continues a similar pathway back into the device via the lower tubules 74, and out into the outlet catheter 70.

Alternatively, all of the tubules may serve as a means for directing the injected substance through the device in one direction, and in that embodiment (not shown), the outlet catheter would be located at the end of the outer casing opposite the inlet catheter. In another embodiment, there may be only the large tubule located within the outer casing thereby forming an inner chamber (embodiment not shown). In an embodiment with a single tubule, the tubule may have one inlet opening, or may have two openings defining an inlet and outlet means.

Figure 4:
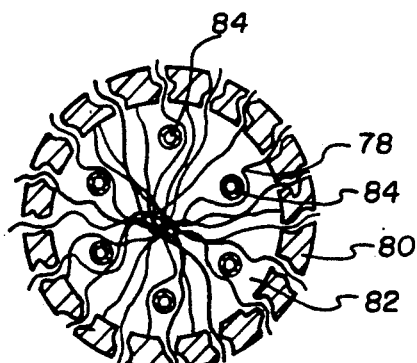
FIG. 4 is a cross-section of the device shown in FIG. 3 taken at line 4—4.

The ingrowth of connective tissue in the device which is illustrated in FIG. 3 can be seen in FIG. 4 where the connective tissue 78 has grown through the pores of the outer casing 80 and into the inner space 82 of the device until it has reached the surface of the tubules 84 therein.

Figure 5:
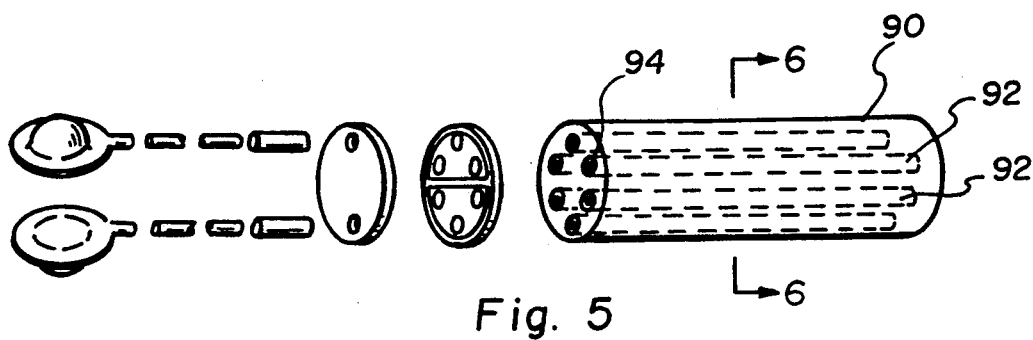
FIG. 5 is a perspective view in partial cutaway illustrating another alternative embodiment of the device.
Figure 6:
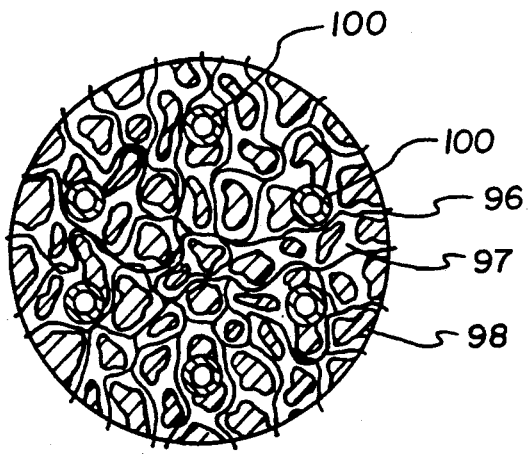
FIG. 6 is a cross-section view of the device shown in FIG. 5 taken at line 6—6.

FIG. 5 illustrates an alternative embodiment of the device which may be designed as a dual-directional flow device, similar to the device illustrated in FIG. 3, or as a unidirectional flow device, similar to the device illustrated in FIG. 1. In this embodiment, the outer casing 90 of porous synthetic material is a solid mass through which linear passageways 92 have been formed. This embodiment differs from those previously described in that the outer casing does not produce an inner space. Hollow tubules 94 of synthetic material, as described in FIG. 3, are placed within the linear passageways formed in the solid outer casing. FIG. 6 illustrates how connective tissue 96 grows through the pores 97 of the outer casing 98 until it reaches the membrane of the tubules 100. In this embodiment, the tubules are placed close to the outer surface of the outer casing to attenuate any encapsulation which may occur otherwise. This embodiment also reduces the occurrence of encapsulation because movement of the ingrown tissue is significantly reduced.

Figure 7:
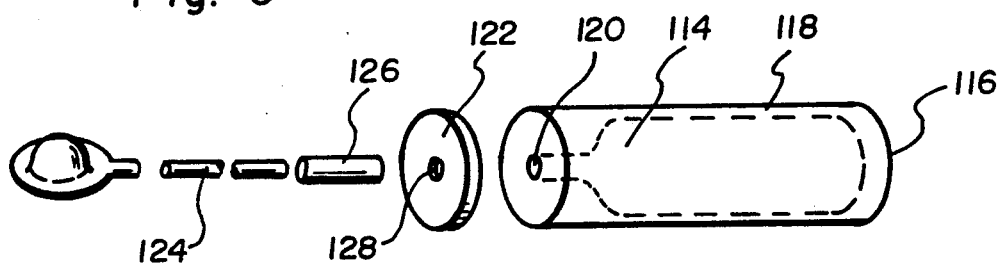
FIG. 7 is an exploded perspective view of another alternative embodiment of the device.

FIG. 7 illustrates another embodiment of the device in which the outer casing 118 defines an inner space 114. The outer casing 118 is closed at one end 116, resulting in a reservoir or chamber being formed by the inner space 114. The open end 120 of the device is covered with a plate 122 having an aperture 128 therethrough for attachment of an inlet catheter 124 and flexible strain connector 126. A drug or substance is injected into the device through the inlet catheter which directs the substance into the inner space 114. There, the drug or substance is diffused into the connective tissue which has grown into the inner space 114.

Figure 8:
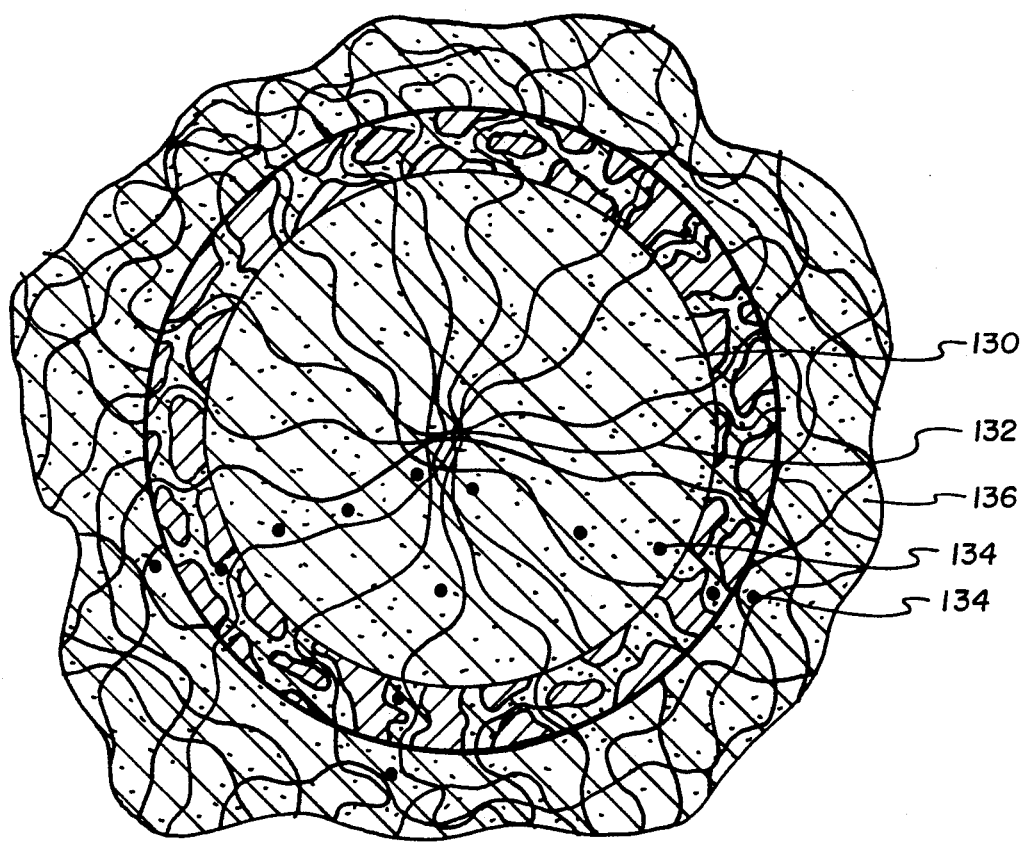
FIG. 8 is a cross-section of the device shown in FIG. 1 illustrating ingrown connective tissue which is vascularized.
Figure 9:
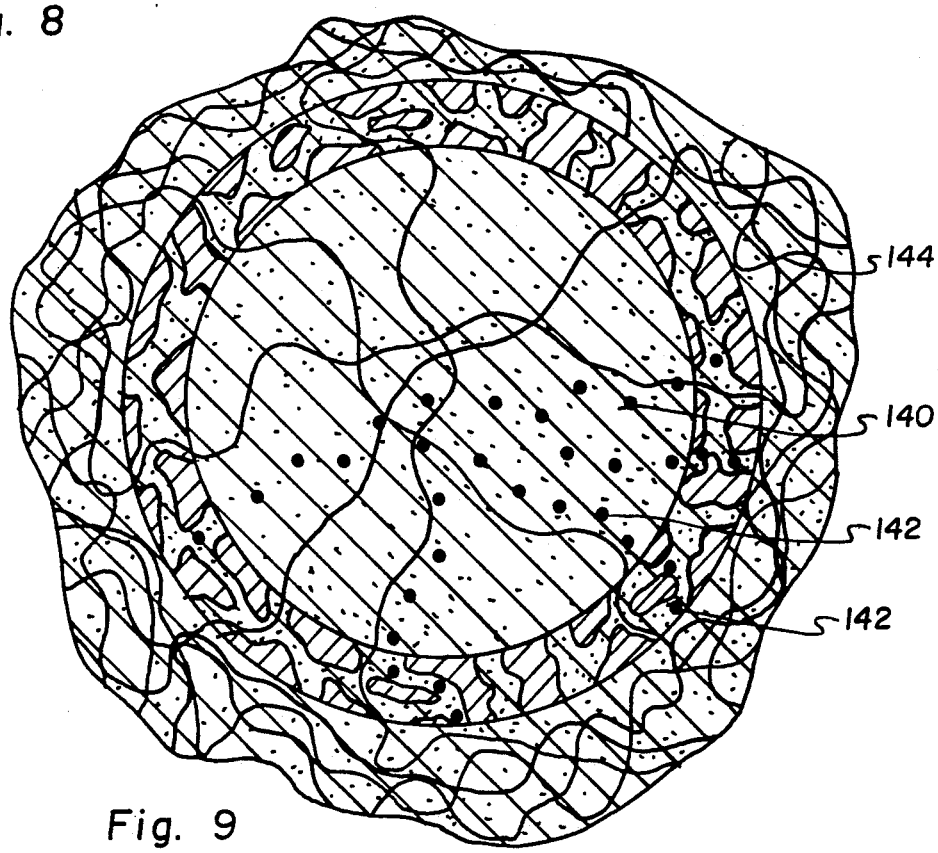
FIG. 9 is cross-section shown in FIG. 1 of the device illustrating matured connective tissue.

Due to the design of the invention, connective tissue is encouraged to grow in a controlled manner through the pores of the outer casing. As a result, the connective tissue remains thin and well-vascularized. With new connective tissue 130, as illustrated in FIG. 8, the vascularization (capillaries) 132 of the tissue serves as the means by which an injected substance 134 may be taken up by the connective tissue and carried out into the omentum 136 of the body. As the connective tissue within the device matures over time, it begins to lose its vascularization. But the tissue is still endowed with interstitial spaces 140 between the individual cells which serve as a means for diffusing injected substances 142 through the tissue and out to the connective tissue pedicle 144 (an area rich in vascularization) surrounding the device, as illustrated in FIG. 9.

A diffusion gradient is produced when any substance or drug is injected into the device, and absorption thereof is so controlled. The amount of substance or drug to be injected is determinable by the required dose of the administration, the volume of the connective tissue (which is in turn dependent upon the dimension of the device), the concentration of the drug or substance, and the pressure (if any) under which the drug may be pumped into the system. Similarly, diffusion rates are determinable by the same criteria.

The embodiments described above serve only as illustrations of the invention and are not intended to limit the scope of the invention which is claimed below.

We claim:

1. An implantable device for administering substances to body tissues of a patient comprising:

an outer casing defining an inner space, said casing being formed of porous synthetic material having pores formed and sized for growth of body tissue through the pores of said synthetic material into said inner space, said outer casing having at least one opening therein which communicates with said inner space; and an inlet catheter of non-porous synthetic material in communication with said opening of said outer casing to form a passageway for conveyance of substance between said inlet catheter and said inner space.

2. The device of claim 1 further comprising an outlet catheter of non-porous synthetic material in communication with an opening of said outer casing to form a second passageway for conveyance of substances between said inner space and said outlet catheter.

3. The device of claim 2 further comprising a pump connected to said inlet catheter for controlled administration of said substances to said inlet catheter.

4. The device of claim 2 further comprising at least one port means connected to said inlet catheter for injecting substances therein.

5. The device of claim 1 wherein said pores of said porous synthetic material range in size from about 60 microns to about 400 microns.

6. An implantable device for administering substances to body tissues of a patient comprising:
   an outer casing of porous synthetic material having pores of sufficient size to allow growth of body tissue therethrough;
   at least one tubule of synthetic material capable of allowing molecules of sufficiently small size to pass through said material while prohibiting growth of body tissue therethrough, said tubule having at least one open end, and said tubule being positioned within said outer casing;
   a first collecting member in communication with said open end of said tubule, said collecting member having at least one aperture therein; and
   an inlet catheter connected to said aperture of said collecting member to form a pathway for substances therebetween.

7. The device of claim 6, further comprising a plurality of tubules, said tubules being substantially parallel to each other within said outer casing.

8. The device of claim 7 wherein each said tubule has a second open end.

9. The device of claim 8 further comprising a second collecting member in communication with each of said second open ends of said tubules to form an intercommunication between said second open ends.

10. The device of claim 9 wherein said second collecting member has an aperture formed therein, said aperture being connected to an outlet catheter for conveyance of substances between said second open ends of said tubules and said outlet catheter.

11. The device of claim 9 wherein said first collecting member has a second aperture to which is connected an outlet catheter for conveyance of substances between said tubules and said outlet catheter.

12. The device of claim 6 wherein said outer casing defines a hollow inner space.

13. The device of claim 6 wherein said synthetic material of said tubule is capable of allowing passage of molecules ranging from a molecular weight of about 10 to a molecular weight of about 100,000.

14. The device of claim 6 wherein said synthetic material of said tubule is capable of prohibiting blood cell components from passing therethrough.

15. An implantable device for administering substances to body tissues of a patient comprising:
   a hollow outer casing of porous synthetic material having pores of sufficient size to allow growth of body tissue therethrough;
   a hollow inner casing of synthetic material capable of allowing molecules of sufficiently small size to pass through said material while prohibiting growth of body tissue therethrough, said inner casing being positioned within said outer casing; and
   an inlet catheter of non-porous material in communication with said hollow inner casing to form a pathway for conveyance of substances therebetween.

16. The device of claim 15 further comprising an outlet catheter of non-porous material in communication with said hollow inner casing to form a pathway for conveyance of substances therebetween.

17. The device of claim 16 further comprising a pump connected to said inlet catheter for controlled administration of substances to said inlet catheter.

18. The device of claim 17 further comprising at least one port means connected to said inlet catheter for injecting substances therein.

19. The device of claim 15 wherein synthetic material of said hollow outer casing range in size from about 60 microns to about 500 microns.

20. The device of claim 15 wherein said synthetic material of said hollow inner casing is capable of allowing passage of molecules ranging from a molecular weight of about 10 to a molecular weight of about 100,000.

21. The device of claim 15 wherein said synthetic material of said hollow inner casing is capable of prohibiting blood cell components from passing therethrough.

22. A method of implanting an implantable device for administering substances to body tissues of a patient comprising:
   obtaining a device comprising an outer casing of porous synthetic material capable of allowing body tissue to grow into the pores of the synthetic material, an inlet catheter and outlet catheter;
   making a surgical incision in the area of the patient where implantation is desired;
   forming a cavity in the tissue area for placement of the device;
   placing the device within the cavity;
   draping excess tissue from the surrounding area about the device to encourage tissue ingrowth;
   securing said excess tissue in place about the device;
   placing said inlet catheter and said outlet catheter in close proximity to the skin of the patient for ease of access postoperatively;
   suturing said inlet catheter and said outlet catheter in place; and
   suturing the incision area closed.

* * * * *